United States Patent [19]

Lobb

[11] Patent Number: 5,214,538
[45] Date of Patent: May 25, 1993

[54] OPTICAL APPARATUS

[75] Inventor: Daniel R. Lobb, Kent, United Kingdom

[73] Assignee: Keymed (Medical and Industrial Equipment) Limited, Southend-On-Sea, United Kingdom

[21] Appl. No.: 720,219

[22] Filed: Jun. 17, 1991

Related U.S. Application Data

[62] Division of Ser. No. 382,746, Jul. 19, 1989, Pat. No. 5,045,936.

[30] Foreign Application Priority Data

Jul. 25, 1988 [GB] United Kingdom ............... 8817672

[51] Int. Cl.⁵ ............................................. G02B 15/14
[52] U.S. Cl. ................................... 359/691; 359/683; 359/692
[58] Field of Search .................. 359/683, 691, 692

[56] References Cited

U.S. PATENT DOCUMENTS

| | | | |
|---|---|---|---|
| 3,576,358 | 4/1971 | Hayamizu et al. | 359/691 |
| 4,425,025 | 1/1984 | Sunaga | 359/643 X |
| 4,488,039 | 12/1984 | Sato et al. | 359/698 |
| 4,874,232 | 10/1989 | Hasegawa | 359/690 |

Primary Examiner—Scott J. Sugarman
Attorney, Agent, or Firm—Beveridge, DeGrandi, Weilacher & Young

[57] ABSTRACT

A laser beam is projected through the optical system of an endoscope and scanned in raster fashion by means of a scanning head at a proximal end of the endoscope tube. The beam is projected from a distal end of the endoscope tube so as to be scanned over an object. Light reflected from the object is detected and used to form a television image. The range of the object is measurable in a ranging mode of the apparatus in which the depth of focus of the projected laser beam is reduced using a zoom lens at the distal end of the endoscope and the focus distance of the projected beam varied until an in-focus position is detected by analysis of the reflected light. Detection of the in-focus position relies on characteristics of laser speckle, a selected portion of the object being scanned in ranging mode to detect maximum modulation in the speckle pattern which occurs when the focus distance corresponds to the range of the object. Range and object size information may then be included in a television image of the object.

6 Claims, 14 Drawing Sheets

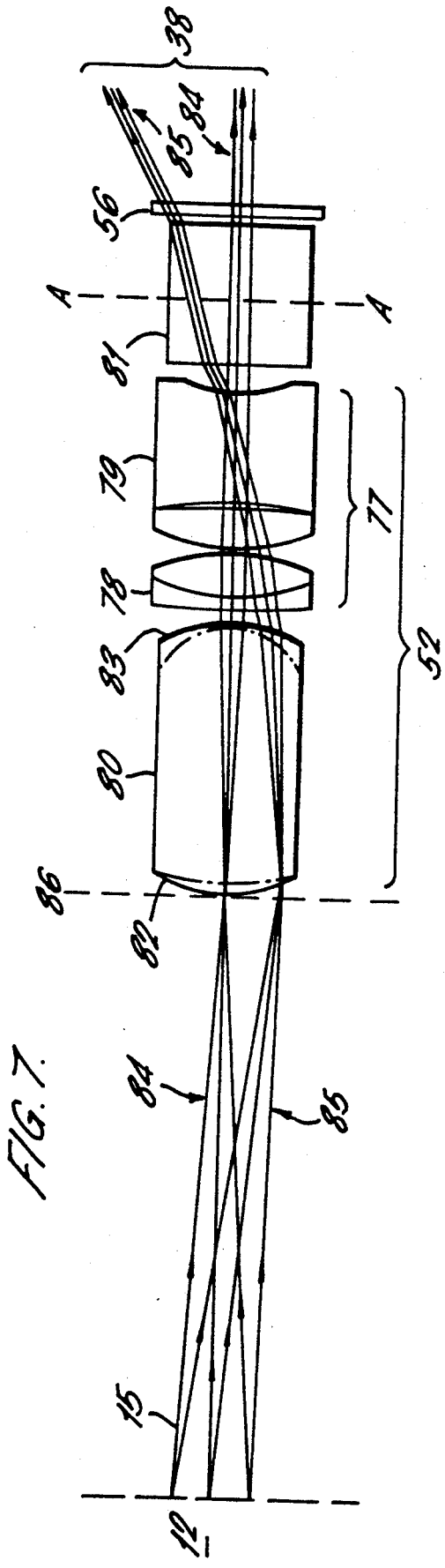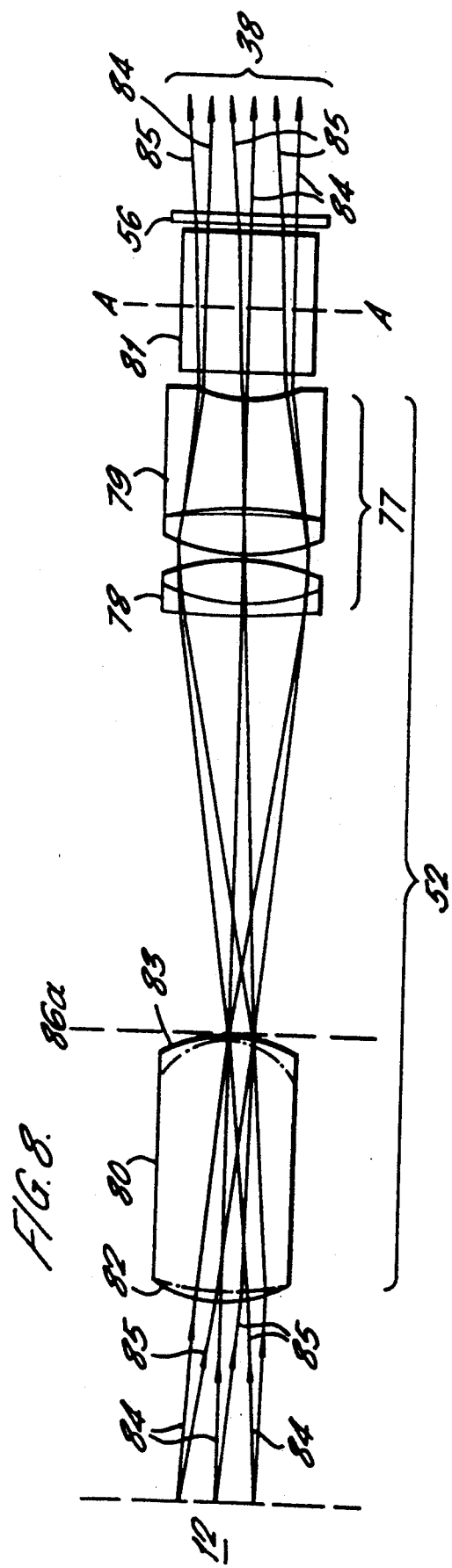
FIG. 7.
FIG. 8.

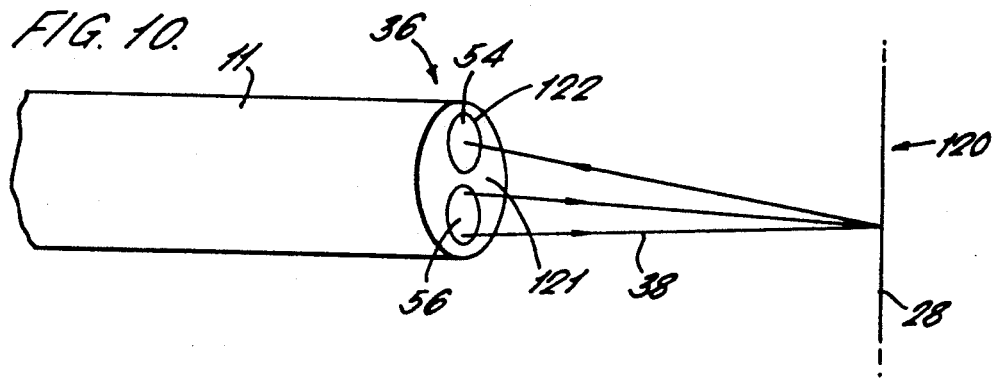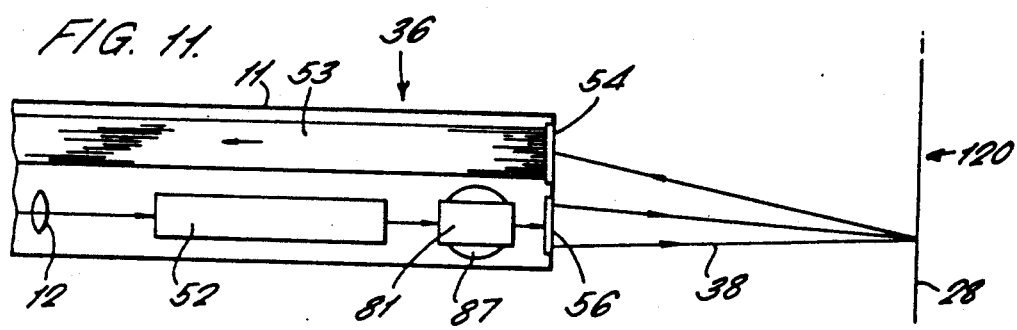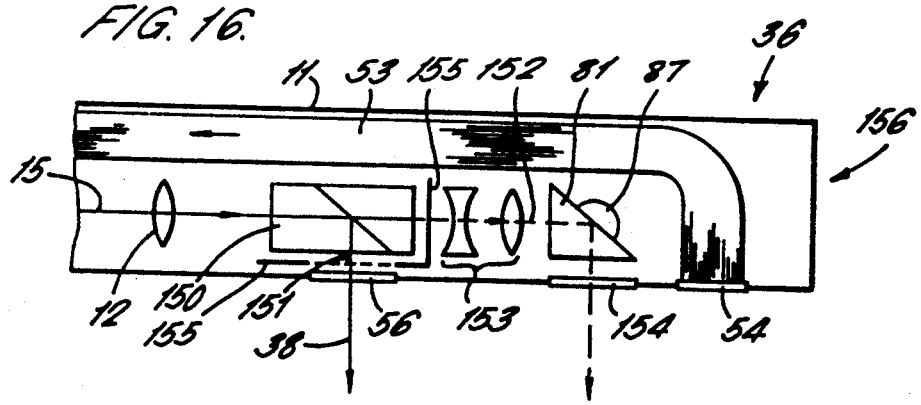

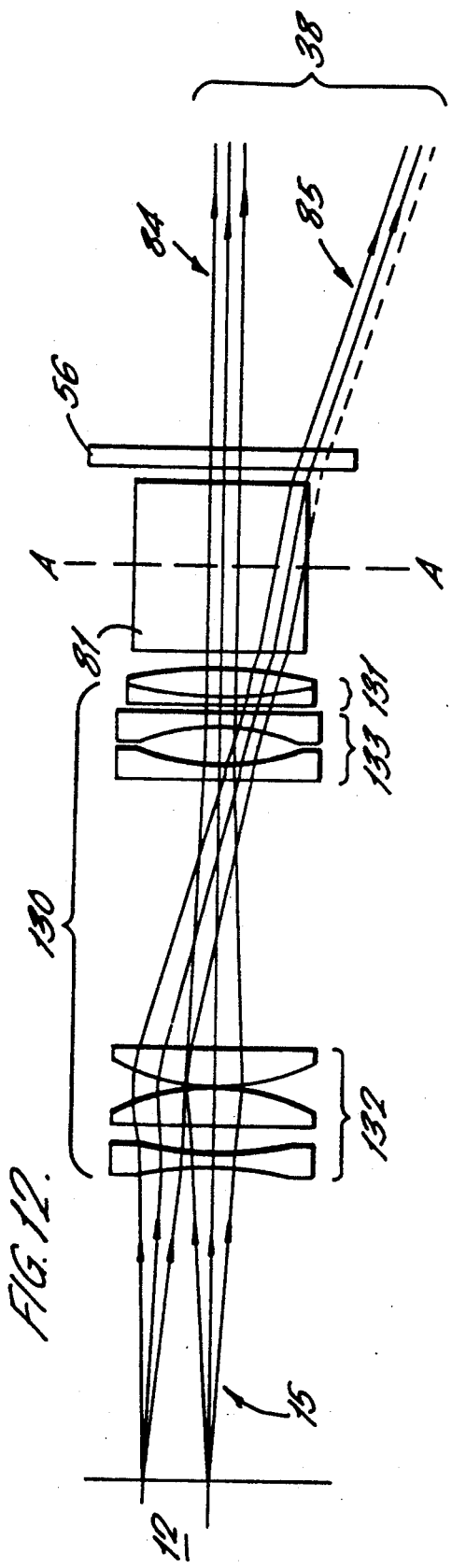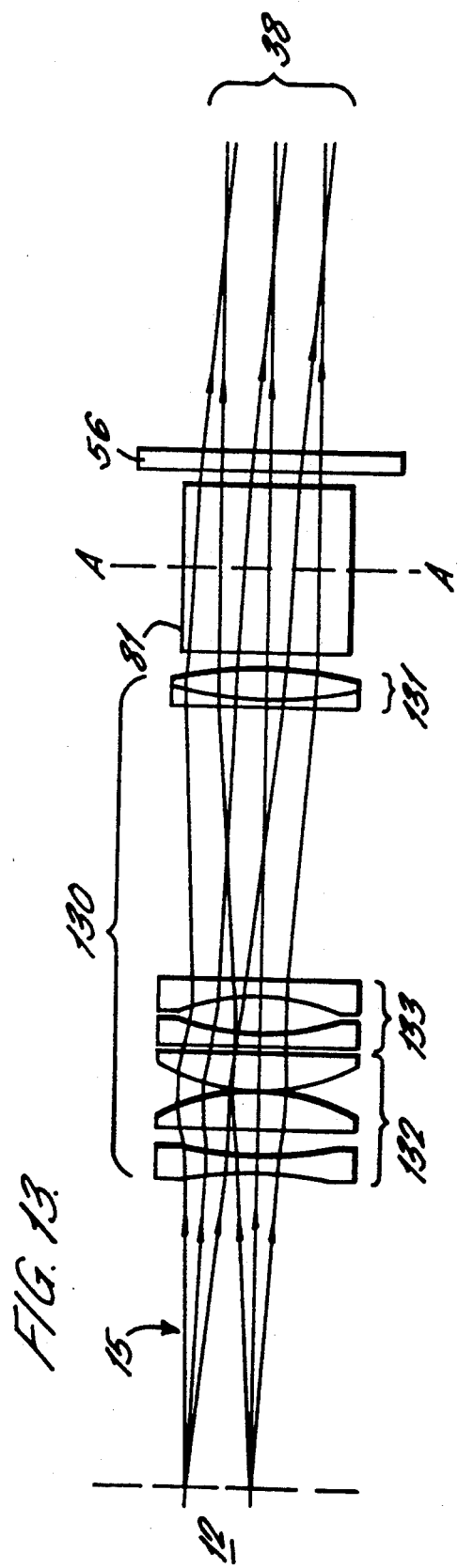
FIG. 12.
FIG. 13.

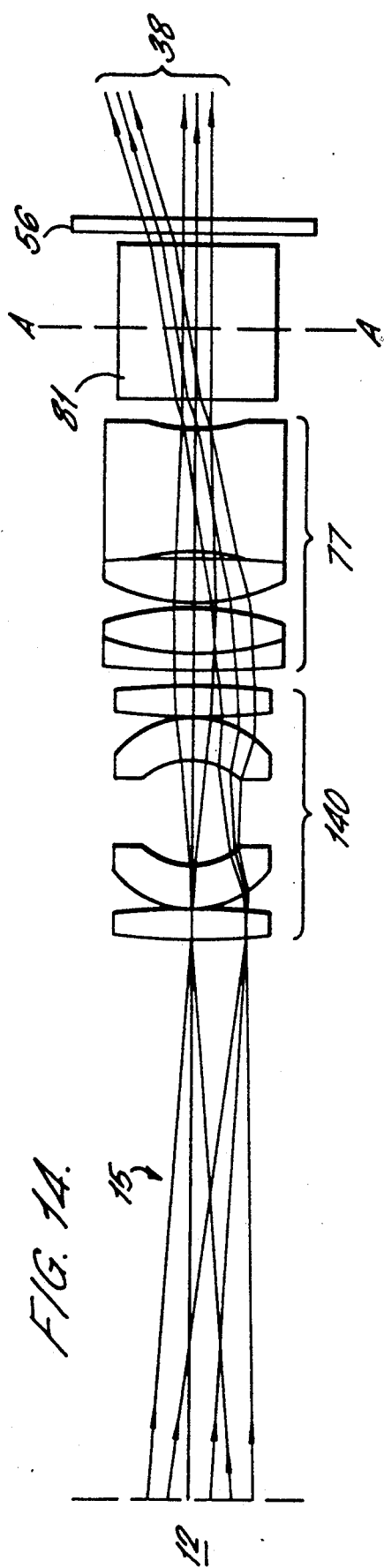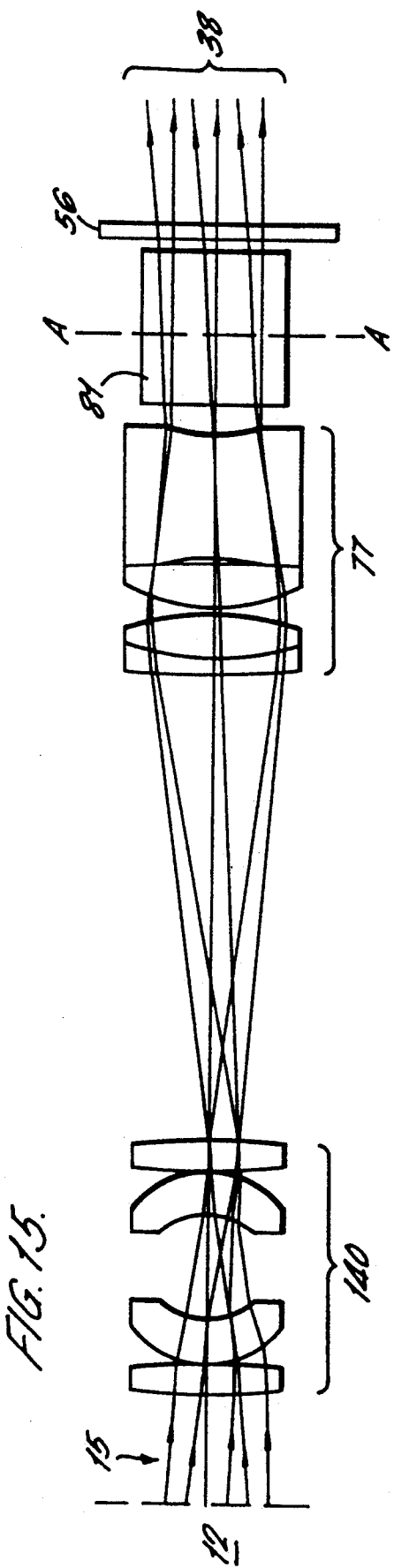

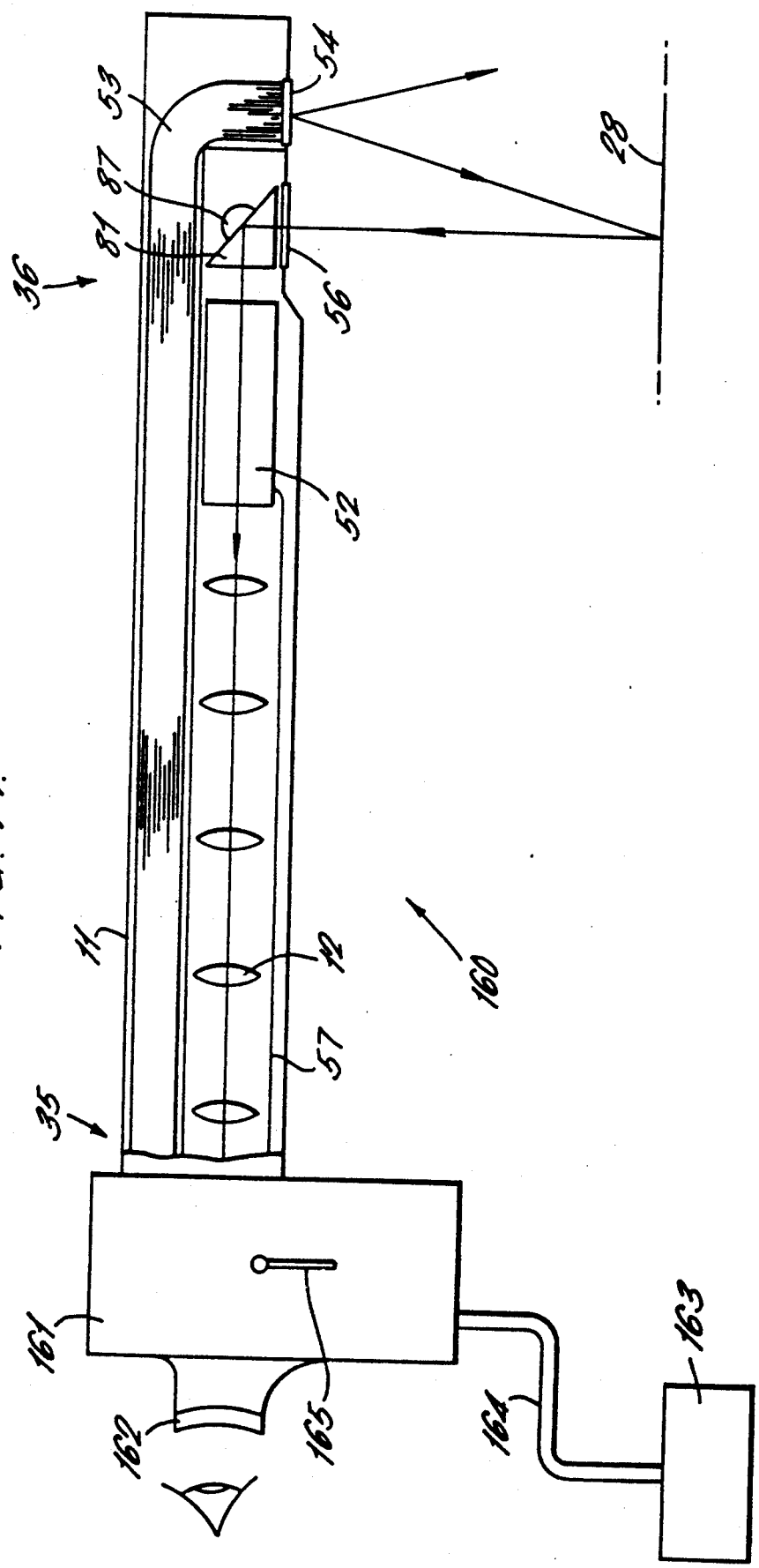

OPTICAL APPARATUS

REFERENCE TO RELATED APPLICATION

This is a division of U.S. patent application 07/382,746, filed Jul. 19, 1989 for Optical Apparatus now U.S. Pat. No. 5,045,936.

The present invention relates to optical apparatus and in particular but not exclusively to electronic endoscopes in which a television image of an object is formed.

Endoscopes are well-known and are used to examine internal surfaces of, for example, human bodies and mechanical components such as engines, aero engines, and aircraft.

Whilst generally satisfactory there are a number of difficulties in utilising known endoscopes. In particular, it can be difficult to obtain an image of sufficient contrast and resolution and furthermore, particularly when an endoscope is being used in an unfamiliar environment, it is difficult to obtain from the image produced an indication of the size of the objects being viewed by the endoscope.

It is known from EP0084435 to improve the contrast and resolution of an optical endoscope by providing means for focusing the optical system of the endoscope in which an intense spot of light is projected onto an object and the focus is adjusted until a clear image of the spot is formed. A disadvantage of such apparatus is that in some applications a high intensity source cannot be used and also the technique is not readily adaptable for use in an electronic endoscope.

It is also known to provide a laser scanning camera for remote inspection purposes in which a laser beam is projected onto an object field and scanned in raster fashion, the reflected beam being detected and used to form a television image. A disadvantage of such cameras is that their bulk inhibits use in confined spaces.

It is also known to use an electronic endoscope to provide a television image in which a solid state detector such as a charge coupled device is mounted at the tip of an endoscope tube. A disadvantage of such endoscopes is that they cannot be used in certain hazardous environments where the tip is to be exposed to high levels of radiation such as in the inspection of nuclear reactors.

Throughout the specification we will refer to "light", "optical" and like expressions. It will be understood, however, that the present invention is not restricted to electromagnetic radiation of visible wavelengths, but may apply to other wavelengths such as infra-red and ultraviolet. The term "lens" used in the specification should also be understood to encompass groups of lens elements where appropriate.

According to the present invention there is disclosed a method of range measurement comprising the steps of passing a laser beam through an optical system so as to be projected into an object field containing an object to be ranged, detecting light reflected from the object, varying the focus distance between an output of the optical system and the position at which the beam is focused by operation of a focus distance varying means, measuring a parameter of the detected light which is characteristic of laser speckle, determining a setting of the focus distance varying means at which the value of the speckle parameter is consistent with the beam being focused onto the object, and determining from calibration of the focus distance varying means the corresponding value of focus distance as a measurement of range.

According to a further aspect of the present invention there is disclosed imaging apparatus comprising an optical system defining an optical axis, a scanning head connected to an input of the optical system, a laser light source connected to an input of the scanning head, the scanning head being operable to project a laser beam into the input of the optical system such that the angle between the beam and the axis is scanned in raster fashion, the optical system having an output comprising a light transmitting window from which the laser beam is projected towards an object field, a light receiving window located adjacent the transmitting window for collecting light reflected from the object field, detection means producing an electrical output signal responsive to light collected by the light receiving window, and electronic apparatus operable to produce a television signal from the detector means output signal whereby a television image of an object in the object field may be obtained, wherein the optical system comprises an endoscope having an elongate tube, the transmitting window and the receiving window being mounted in a distal end of the tube for insertion into inaccessible areas, and the optical system including an optical relay through which the optical axis extends longitudinally within the tube.

According to a further aspect of the present invention there is disclosed an optical assembly comprising an objective lens and a field lens which is movable relative to the objective lens between a first position adjacent the objective lens and a second position spaced from the objective lens, the field lens and objective lens in combination defining a focal plane which is at the same location relative to the objective lens for both first and second positions of the field lens and wherein the field lens passes through the focal plane in moving between the first and second positions.

An apparatus including an endoscope illustrating a preferred embodiment of several aspects of the invention will now be described by way of example only and with reference to the accompanying drawings in which:

FIG. 7 is a diagram showing a zoom lens of the endoscope of FIG. 3;

FIG. 8 is a diagram of the zoom lens of FIG. 7 in its ranging configuration;

FIG. 10 is a perspective view of the proximal end of a forward viewing endoscope in a modified apparatus;

FIG. 11 is a schematic plan of the proximal end of the apparatus of FIG. 10;

FIG. 12 is a schematic view of a conventional zoom lens incorporated in a modification to the apparatus of FIG. 3;

FIG. 13 is a schematic view of the zoom lens of FIG. 12 in its ranging configuration;

FIG. 14 is a schematic view of a further zoom lens with field curvature correction;

FIG. 15 is a schematic view of the zoom lens of FIG. 14 in its ranging configuration;

FIG. 16 is a schematic plan of a proximal end of a modification to the apparatus of FIG. 3 in which the zoom lens is replaced by a fixed lens system and optical switching means;

FIG. 17 is a schematic view of an otherwise conventional endoscope modified to include a zoom lens;

Figure 1:
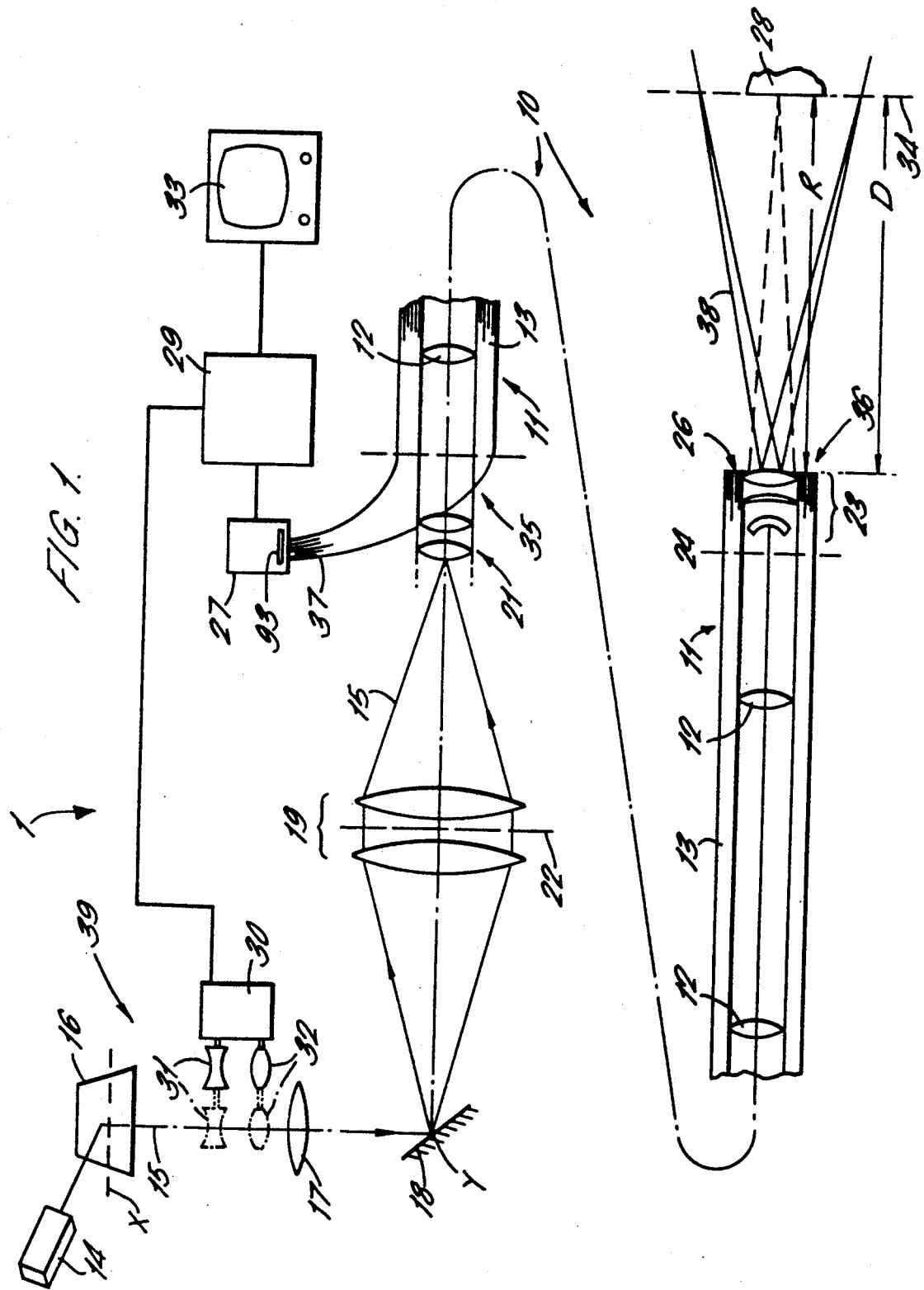
FIG. 1 is a folded side view of apparatus including a forward viewing endoscope.
Figure 2:
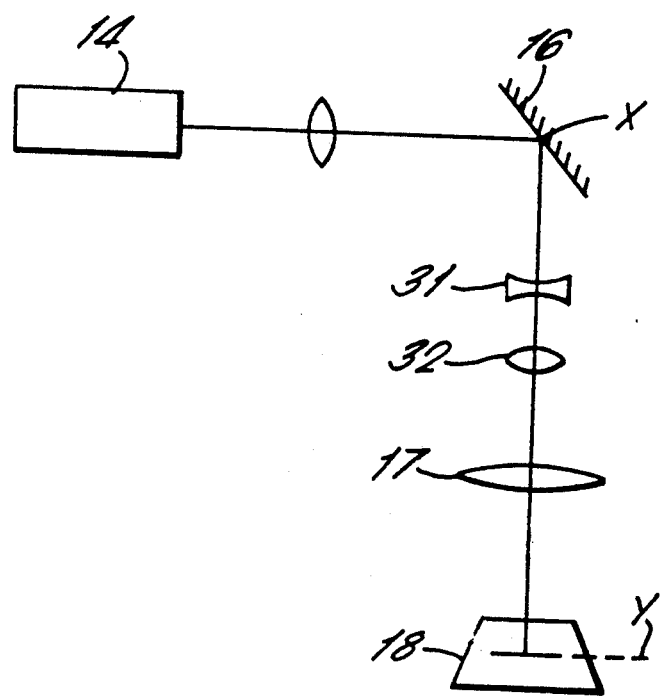
FIG. 2 is an end view of part of the apparatus of FIG. 1.

Referring to FIGS. 1 and 2 there is shown in diagrammatic sketch form an apparatus comprising an endoscope 10.

In FIG. 1 the length of endoscope 10 is chosen for the particular purpose required. The endoscope 10 comprises a rigid hollow tube 11 of 10 mm diameter containing an optical relay comprising a series of relay lenses 12 spaced along the tube so that the image plane of one coincides with the object plane of the next lens in the series.

Surrounding the optical relay is a longitudinally extending fibre optic bundle 13 of annular cross-section.

The endoscope 10 has a distal end 36 presented to an object 28 to be viewed and a proximal end 35 at which there is provided a laser scanning head 39 including a laser 14. A laser beam 15 passes from the laser 14 to a first scanning mirror 16 which is pivoted for scanning through a small angle about an axis X passing through the point at which the laser beam 15 strikes the mirror 16 such that the beam 15 is at 45° to the mean position of the mirror. The beam reflected from the scanning mirror 16 passes to a second scanning mirror 18 via a lens 17, which mirror 18 is pivoted for scanning through a small angle about an axis Y at right angles to the axis X such that the beam is at 45° to the mean position of the mirror.

The beam 15 reflected from the second scanning mirror 18 passes to a collecting lens group 19 comprising two spaced apart lenses directing the beam into the proximal end 35 of the endoscope 10 where it enters an input lens 21 of the optical relay 12.

The lens 17 is arranged so as to bring the laser beam 15 into focus in an image plane 22 located between the two lenses of the lens group 19 so that any dust on the lens surfaces does not interfere with the image. This image plane 22 is arranged to be the object plane of the first lens 21 of the optical relay lenses 12.

An output lens assembly 23 is provided at the distal end 36 of the endoscope 10 and has a projected image plane 34 which is illustrated in FIG. 1 as being coincident with the object 28.

A light collecting input surface 26 of the fibre optic bundle 13 surrounds the output lens assembly 23 and faces the object 28 so that light reflected from the object is collected at the surface and passes into the fibre optic bundle. The collected light is conveyed along the fibre optic bundle 13 to a photomultiplier 27 connected by a fibre optic link 37 to the proximal end 35 of the endoscope 10.

An interference filter 93 transmitting light only at the laser frequency is placed in front of the photomultiplier 27 to remove effects of ambient light.

The output signal from the photomultiplier 27 is passed to an electronic apparatus 29 which is synchronised with the scanning mirrors 16,18 to form a television image viewed on a television monitor screen 33.

In addition to the described components there is provided in the scanning head 39 a pair of lenses 31,32 which may selectively be moved into and out of the path of laser beam 15 between the first scanning mirror 16 and lens 17, this movement and their exact positions along the optical axis being controlled by a motor system 30. In FIG. 1 the lenses 31,32 are shown in broken lines at their positions when moved into the path of the laser beam 15 and are shown in unbroken lines at their normally retracted positions in which they are clear of the path of the laser beam 15.

The lenses 31,32 consist of a diverging lens 31 followed by a converging lens 32 which when introduced into the optical path have the effect of broadening the beam such that on emerging from the distal end 36 a projected laser beam 38 fills the aperture defined by the output lens 23. When retracted from the optical path the effective aperture of the apparatus 1 is reduced or in other words the beam 38 remains relatively narrow and is projected from the output lens 23 with a reduced convergence angle. Axial movement of the lenses 31,32 provides movement of the focal plane 34 at which the projected beam 38 is focused.

In use of the apparatus 1 the laser beam 15 is scanned horizontally and vertically across the image plane 22 by means of the first and second scanning mirrors 16,18 respectively in a raster form. Thus, a spot image of the beam 15 formed in the image plane 22 moves horizontally line by line and slowly vertically downwards as in a television picture. The limits of the range of movement of the beam 15 are generally illustrated in FIG. 1, but it will be understood that at any one time the beam 15 is deflected to a single point in the image plane 22. The terms vertical and horizontal used with reference to the raster scan are relative and do not necessarily comply with those particular directions in space.

The raster scan of the beam 15 is transmitted from the image plane 22, which forms the object plane of the first lens 21 of the optical relay 12, and hence is passed into the endoscope 10 and is transmitted through the endoscope to the object plane 24 of the output lens assembly 23. The projected laser beam 38 is then projected from the endoscope through the output lens assembly 23 so as to scan across the object 28 to be viewed in raster fashion (the beam at this point in FIG. 1 being shown in solid lines).

Thus, as the laser beam 38 scans across the object 28 reflected and scattered light is collected by the input surface 26 of the fibre optic bundle 13. The collected light passes down the fibre optic bundle 13 and is detected by the photomultiplier 27.

The photomultiplier 27 at any one time produces a single signal dependent upon the total amount of light entering the input surface 26.

The output signal from the photomultiplier 27 is passed to the electronic apparatus 29 and a corresponding image point is generated on the screen 33 which scans at the same rate and in the same way as the beam 38 is scanned across the object 28. Thus a composite image of that object 28 will be produced on the television screen 33 in each completed frame of the scan.

There are a number of advantages of producing a composite image in this manner. By the use of a laser beam, the light flux illuminating each element of the object under examination can be high. All of the light is concentrated on the spot, rather than generally illuminating the object under examination.

Because of the small convergence angle of the projected beam during imaging it is possible to have great depth of focus which reduces the aberration effects.

Similarly, the use of a laser enables the detected signal to have an inherently high signal to noise ratio. A monochromatic laser source can be matched to the coatings on the lenses so as to reduce to a very small level the reflection of the beam from the surface of the lenses and, indeed, the lenses themselves can be matched to the particular wavelength of the laser beam.

Furthermore, a clear high contrast high resolution image can be provided with relatively low input of total energy to the object under examination which is a considerable advantage in some applications, for example medical applications. Other applications include imaging of hazardous environments where high energy illumination must be avoided because of the flammability of vapours for example.

The apparatus 1 may also be used to measure and display information as to the range and size of objects imaged on the screen 33. This is particularly useful when the user is unfamiliar with the object being viewed so that it is difficult to gauge an impression of size from the television image in which a small object at a short range could appear to have the same size as a large object at a greater range.

The apparatus 1 is used to measure range of a viewed object 28 in its range finding mode in which lenses 31 and 32 are introduced into the path of laser beam 15. The range finding procedure requires that the focus distance D between the focal plane 34 and the distal end 36 be varied until an analysis of the output of photomultiplier 27 indicates that the object 28 is in focus i.e. that the projected laser beam 38 is focused on to a surface of the object 28. Movement of the focal plane 34 is accomplished by axial movement of the lenses 31 and 32. Analysis of the output of the photomultiplier 27 to determine the in-focus condition relies upon the phenomenon of laser speckle which is the random intensity distribution exhibited in light observed in non-specular reflection of a laser beam and results from constructive and destructive interference of coherent waveforms reflected from surfaces which are rough on the scale of the wavelength used. It is observed that the speckle pattern which appears on the reflecting surface changes as the beam is brought in and out of focus. Both the spacial frequency and amplitude of intensity modulation are seen to vary, the amplitude of modulation being at a maximum when the beam is in focus.

Speckle is detected in the output of the photomultiplier 27 as a strong AC modulation during a horizontal scan which is readily distinguishable from the less noisy DC signal resulting from a scan of the same object when the laser beam is out of focus. The beam is taken to be focused on the object when the amplitude of modulation is at a maximum. The frequency of modulation depends upon the rate at which the projected beam traverses the object surface, the distance across the reflecting surface traversed in one cycle of modulation being of the same order of magnitude as the cross-section of the projected beam 38 measured at the output lens assembly 23.

Effectiveness of the range finding mode is enhanced by the increased effective aperture resulting from insertion of the lenses 31 and 32 since this results in a marked decrease in the depth of focus of the projected beam 38.

The projected beam 38 in ranging mode of the apparatus 1 is shown in broken lines in FIG. 1 in which it is focused on to the object 28.

The distance D corresponding to the position of lenses 31 and 32 is then computed by the electronic apparatus 29 and displayed on screen 33 as a measurement of range R between the object 28 and the distal end 36. It is then possible to measure the width of a particular object at that distance by measuring the width of the image of the object on the screen 33 and multiplying this width by a conversion factor based on calibration measurements.

During ranging the pivotal movement of the scanning mirror 16 is stopped. In addition, because it is necessary to range over only a small part of the object, (since otherwise a variable range will be provided) the scanning movement of the mirror 18 is restricted.

The beam used during the ranging operation is illustrated by broken lines in FIG. 1 and as can be seen it is considerably wider at the lens assembly 23 than the beam represented in unbroken lines used during normal imaging.

It has been found optimum to arrange that the overall cross-section of the input surface 26 of the optical fibres 12 is the same as the cross-sectional area of the projected beam 38 at the output lens assembly 23 during the ranging operation and under these circumstances it has been found that as the focal plane 34 is moved back and forth (by relative movement of lenses 31 and 32) the modulation due to speckle in the signal detected by the photomultiplier 27 is at a maximum when the plane 34 coincides with the surface of the object 28.

As a result, this provides an automatic method of ranging in which movement of the lenses 31,32 to move the plane 34 is controlled by the motor system 30, the operation of which is under control of the electronic apparatus 29. Thus, in use, the electronic apparatus 29 causes the lenses 31,32 to move the plane 34 until the modulation of the signal detected by the photodetector 27 is a maximum. At that point the electronic apparatus 29 is able to determine the range R, that is the distance between the distal end 36 of the endoscope 10 and the object 28, by reference to stored data of focus distance D as a function of the position of lenses 31 and 32 from previous calibration experiments. When switched back to viewing mode the screen 33 may then carry, in addition to an image of the object 28, a scale from which the size of the object 28 may be directly measured.

To prevent mismeasurement, the arrangement may be such that when the endoscope 10 is moved the scale on the screen 33 disappears, since at that point a new ranging will be required.

The invention is not restricted to the details of the foregoing example. In particular in relation to the latter inventive concept, it would clearly be useful to regularly range and view. Thus, it may be provided that the lenses 31,32 are regularly moved into the beam path. Alternatively the beam path itself may be split so as to pass, in one parallel beam path through the lenses 31,32 and in the other not through those lenses, optical switching means being provided to switch back and forth between these two paths whereby the ranging can be regularly carried out. Hence the scale can be shown on the screen 33 continuously although it will vary continuously as the endoscope 10 is moved with respect to the object 28.

The fibre optic bundle 13 is shown in FIG. 1 as being annular but in an alternative arrangement the bundle may be of generally circular cross-section.

The ranging and hence scaling of the image has been described with respect to an endoscope 10. Clearly, however, this aspect of the invention may be applicable to other optical systems such as microscopes, telescopes and other scanning systems.

Figure 3:
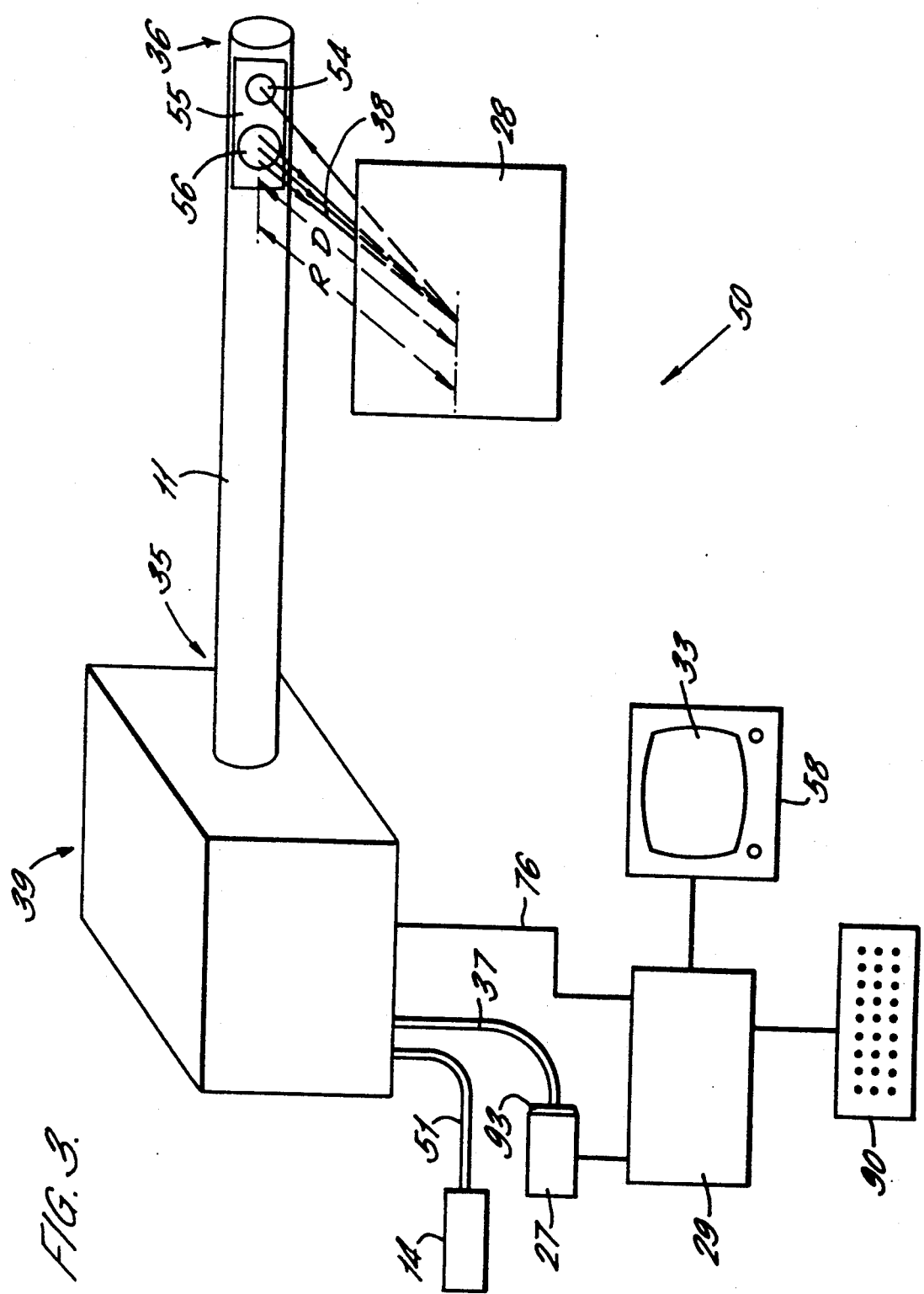
FIG. 3 is a schematic view of an alternative apparatus including a side viewing endoscope.

A further embodiment of the invention is shown in FIG. 3 in which corresponding reference numerals are used to those of FIGS. 1 and 2 where appropriate for corresponding elements.

The alternative apparatus 50 of FIG. 3 comprises a rigid endoscope tube 11 having a distal end 36 which is insertable into inaccessible areas for imaging purposes and is shown being directed towards an object 28.

The endoscope tube 11 has a proximal end 35 connected to a laser scanning head 39. A flexible single mode fibre optic link 51 connects a laser 14 to the laser scanning head 39, the link 51 comprising a single optical fibre which retains the coherence characteristics of the light carried.

Figure 4:
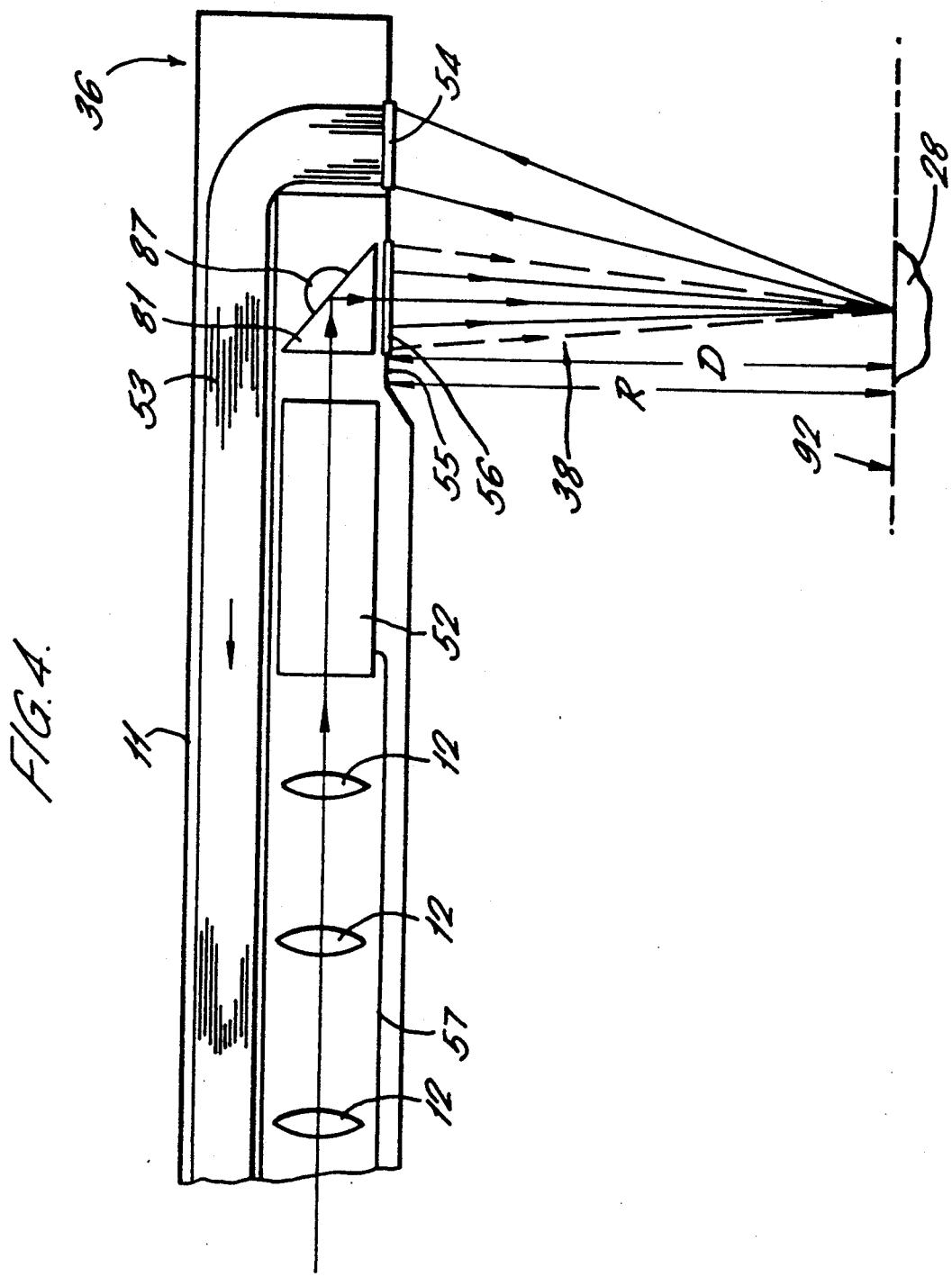
FIG. 4 is a detail of the tip of the endoscope of FIG. 3.

As shown in FIG. 4 the endoscope tube contains an optical relay 12 for conveying a raster scanned laser beam from the laser scanning head 39 to a zoom lens assembly 52. A right angle prism 81 is arranged to deflect light emerging from the zoom lens assembly 52 so as to exit through a window 56 provided in a side wall 55 of the tube 11 as a projected laser beam 38.

The prism 81 is provided with a prism rotating mechanism 87 capable of tilting the prism about a vertical axis to produce horizontal deflection of the field scanned by the projected beam 38. Tilting of the prism 81 is actuated by a control wire (not shown) connected to an actuator (not shown) in the scanning head 39. Vertical deflection of the field scanned by the projected beam 38 is provided by rotation of the tube 11 about its longitudinal axis by means of a tube rotating mechanism (not shown). As described later, the prism rotating mechanism 87 and tube rotating mechanism provide means for varying the direction of the optical axis at the window 56 when the projected beam 38 is to be directed onto a selected area of the object which would otherwise be located outside of the reduced field angle available in ranging mode.

A fibre optic bundle 53 extends longitudinally through the tube 11 and terminates in a circular light collecting surface 54 forming part of the side wall 55.

The light collecting surface 54 is positioned side-by-side relative to the window 56 so that the apparatus 50 constitutes a side viewing endoscope.

Figure 5:
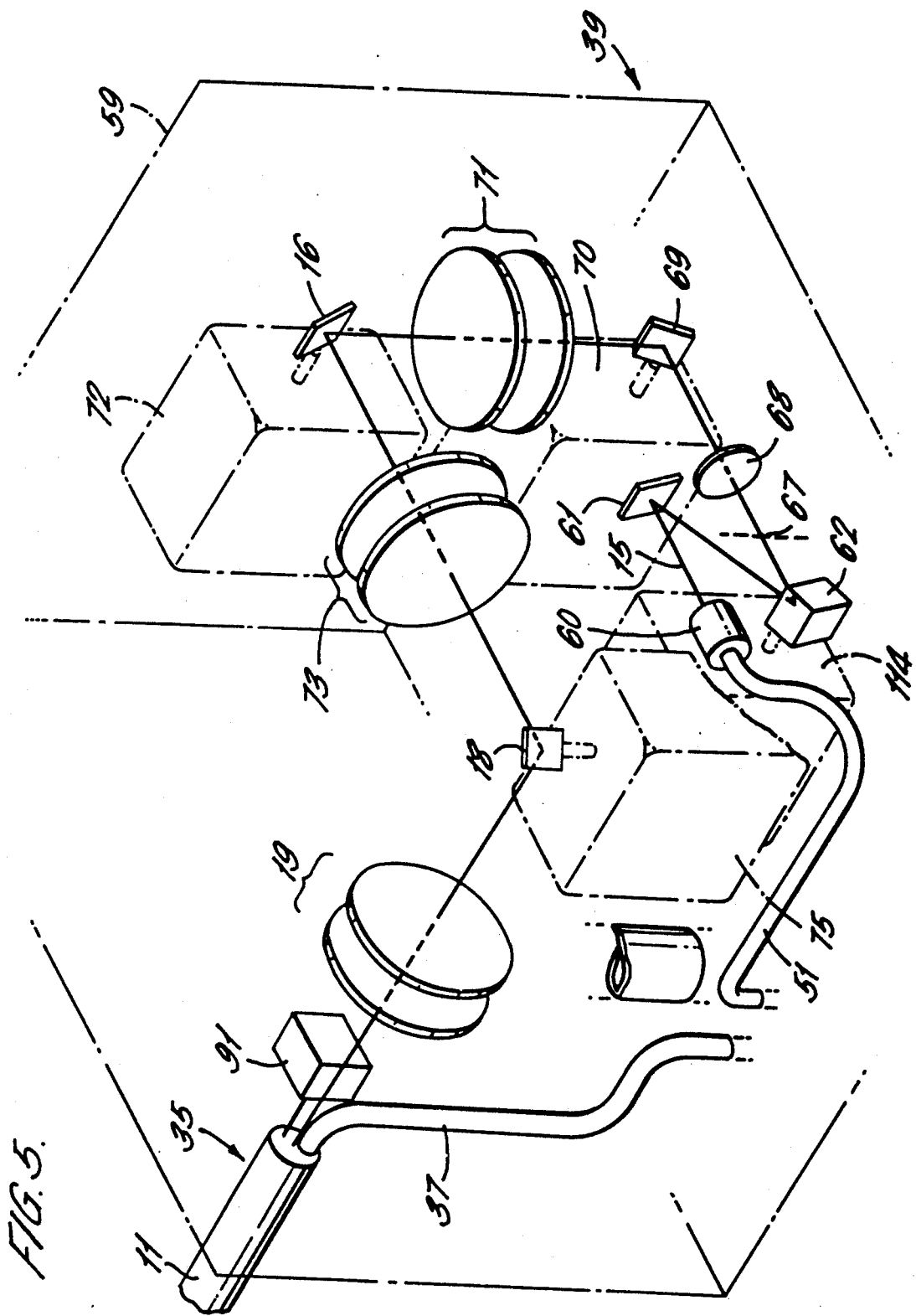
FIG. 5 is a perspective view of the internal components of a scanning head of the apparatus of FIG. 3.

A control wire 57 extends through the tube 11 and connects the zoom lens assembly 52 with a linear drive mechanism 91 shown in FIG. 5 in the laser scanning head 39.

A fibre optic link 37 connects the scanning head 39 to a photomultiplier 27, the connection being such that substantially all of the light collected at the surface 54 is conducted to the photomultiplier. An interference filter 93 transmitting light only at the laser frequency is positioned in front of the photomultiplier 27 to remove the effects of ambient light. An output signal from the photomultiplier 27 is input to an electronic apparatus 29 which in turn produces a signal driving a television monitor 58 having a screen 33.

The construction of the laser scanning head 39 is illustrated in FIG. 5 and comprises a housing 59 to which is rigidly connected the endoscope tube 11. The fibre optic link 37 is shown projecting from the proximal end 35 of the tube 11.

The single mode fibre optic link 51 carrying the laser beam from laser 14 enters the housing 59 and has a terminal 60 which incorporates a converging lens (not shown). A laser beam 15 emerges from the terminal 60 and is represented in the drawing by a single line extending along the optical axis of the scanning head 39 whereas in practice the beam will have finite width and convergence.

Figure 6:
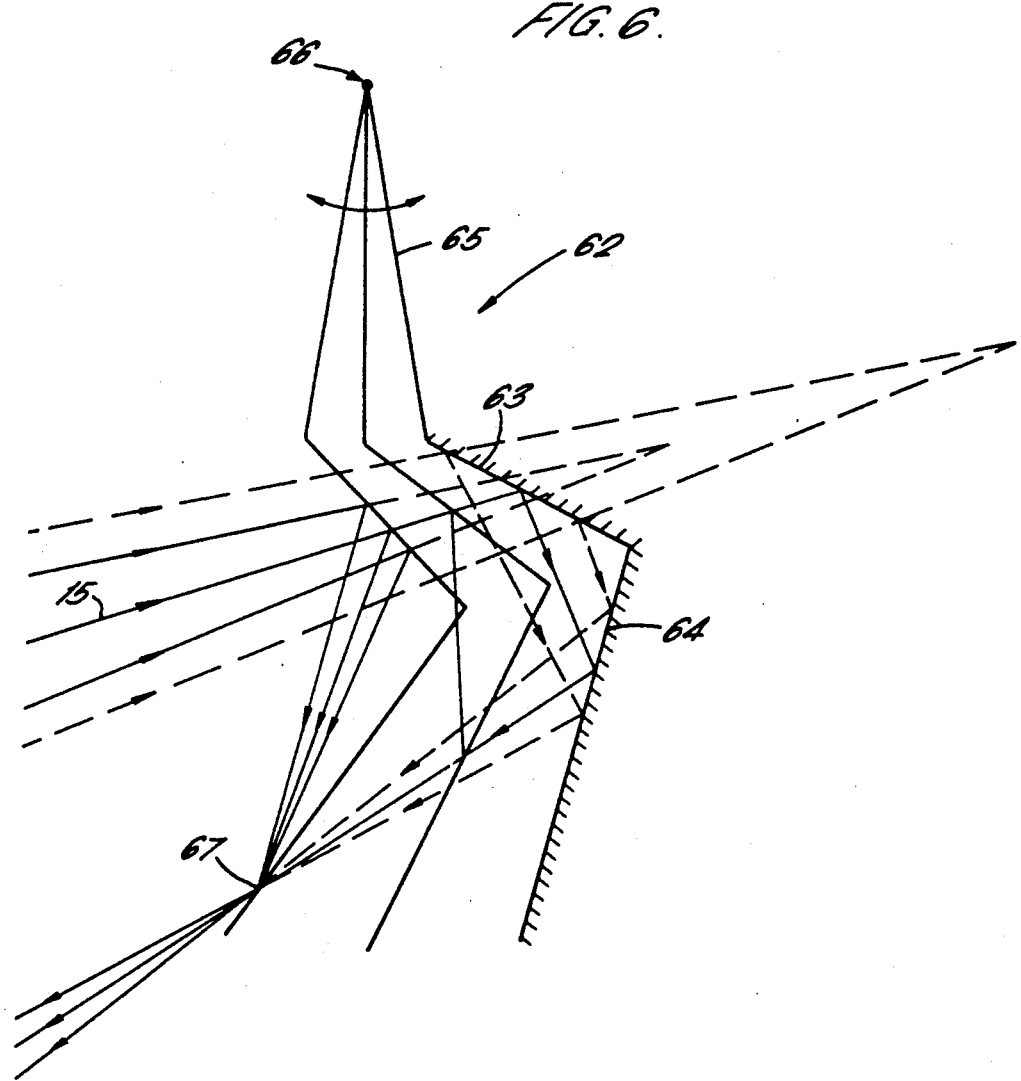
FIG. 6 is a schematic diagram of a mirror system of the scanning head of FIG. 5.

The beam 15 is directed on to a plane mirror 61 which is provided to fold the light path and direct the beam into a mirror system 62 represented schematically as a cube in the drawing. The mirror system 62 is shown in FIG. 6 and consists of two orthogonal mirrors 63 and 64 which are fixed relative to each other and mounted at the end of a radius arm 65 providing rotation about a pivot 66. A motor drive and transducer responsive to angular position (not shown) are provided by a range scanning unit 114 (see FIG. 5) for controlling the angular position of the mirrors 63 and 64. The effect of shifting position of the mirrors by pivotal motion is to increase or decrease the path length travelled by the converging laser beam 15. Consequently the mirror system 62 provides a means of shifting along the optical axis an image position 67 at which laser beam 15 is focused by the lens of the terminal 60. This in turn enables the focus distance D at which the projected beam 38 is focused relative to the window 56 to be dynamically varied.

The laser beam 15 on leaving the mirror system 62 passes through a converging lens 68 to a scanning mirror 69 arranged to produce scanning motion in the horizontal direction in the projected beam 38 emerging from the end window 56. The scanning mirror 69 is driven by a galvanometer type scanning unit 70 capable of positioning the mirror in any required position in a randomly addressable mode. This facility is required during ranging operation as described later.

The beam is then directed by a lens pair 71 to a further scanning mirror 16 driven by a further scanning unit 72 of a resonant galvanometer type producing horizontal line scan in the projected beam 38 a horizontal scanning frequency of 8 kHz. A cable 76 (represented in FIG. 3) connects the scanning head 39 to the electronic apparatus 29 and carries control signals.

From the scanning mirror 16 the beam 15 is relayed by a lens pair 73 to a final scanning mirror 18 driven by a final scanning unit 75 of a galvanometer type mechanism providing accurate control of the mirror position in a randomly addressable manner. The final scanning mirror 18 is arranged to produce vertical scanning of the projected beam 38.

A further lens pair 19 directs the scanned beam 15 into the optical relay 12 so that the beam is directed through the endoscope tube 11 into the zoom lens assembly 52.

The zoom lens assembly 52 is illustrated in detail in FIGS. 7 and 8. The lens assembly 52 is referred to as a "zoom" lens assembly to convey the meaning that the lens assembly has a variable focal length. In the present context it is intended that the focus need not be continuously variable. The present requirement is that the lens assembly should provide two possible configurations giving different focal lengths and hence two possible values of angular magnification, for each of which configurations the optics are well corrected in terms of aberrations. The zoom lens assembly 52 in its normal configuration when the projected beam 38 is being scanned for imaging purposes provides a field angle of 50° over which the beam is scanned both horizontally and vertically. This configuration will be referred to as the imaging configuration of the zoom lens assembly 52.

The zoom lens assembly 52 has a second configuration which will be referred to as the ranging configuration in which the field angle is reduced to 10°. In the imaging configuration the convergence angle of the projected beam 38 is relatively small as shown in solid lines in FIG. 4 whereas in the ranging configuration the projected beam 38 fills the aperture defined by the end window 56 and has a greater convergence angle and consequently provides a reduced depth of field during ranging.

The zoom lens 52 is shown in its imaging configuration in FIG. 7 and in its ranging configuration in FIG. 8. The zoom lens 52 comprises a fixed lens 77 of positive power and comprising compound lens elements 78 and 79. An axially movable lens 80 is located between the fixed lens 77 and the optical relay 12 so that the laser beam 15 passes from the optical relay, through the movable lens and then through the fixed lens 77. A right angle prism 81 deflects the beam 15 emerging from the fixed lens 77 through 90°, the light rays drawn to the right of line A—A should therefore be imagined as travelling in a plane orthogonal to the page.

The movable lens 80 and the fixed lens 77 constitute a field lens and objective lens respectively of the zoom lens.

The movable lens 80 is formed of BK7 glass and comprises a convex single thick element of 9.56 mm thickness having the same magnitude of curvature (0.17357 mm-1) on both its front and rear optical faces 82 and 83 respectively.

A fixed lens 77 comprises (from left to right in FIGS. 7 and 8) an element of SK10 glass of 1.5 mm thickness and curvature 0.11717 and −0.10386; an air gap of 0.10; an element of SK10 glass of thickness 1.50 and curvature 0.16440 and −0.00530; a further air gap of 0.10; an element of SK10 glass with thickness 4.0 and curvature −0.03633 and 0.20974; and an air gap of 1.0 following by the prism 81 (all dimensions of separations being in mm and curvature in mm-1)

The beam 15 is represented by groups of pencil rays 84 and 85 which correspond respectively to a beam projected along the optical axis of the apparatus 50 and a beam which is deflected by the scanning head 39 so as to form a projected beam 38 which is vertically deflected to the maximum limit available.

The optical relay 12 projects a real image at an image plane 86 which in the imaging configuration of the zoom lens 52 coincides with the front face 82 of the movable lens 80 which is also arranged to coincide with the focal plane of the zoom lens 52 i.e. the combination of the movable lens 80 and fixed lens 77.

In this configuration a wide field angle is provided by the zoom lens 52 so that the vertical and horizontal scan in each case covers 50°.

In FIG. 8 the zoom lens 52 is shown in its ranging configuration in which the moving lens 80 has been moved away from the fixed lens 77 so as to pass through the image plane 86 projected by the optical relay 12 to a new position in which the real image plane 86a coincides with the rear face 83 of the movable lens 80.

The image plane 86 is translated by the presence of the movable lens 80 in a direction towards the optical relay 12 but in its new position 86a as shown in FIG. 8 is coincident with the focal plane of the fixed lens 77.

In FIG. 8 three pencil rays 84 represent the laser beam projected by the scanning head 39 along the optical axis of the apparatus 50 and pencil rays 85 represent the beam when vertically deflected to the maximum available limit.

In both FIGS. 7 and 8 the pencil rays 84 and 85 are drawn in the case where the projected beam 38 is collimated i.e. focused at infinity so that for each position of the movable lens 80 the image plane 86 corresponds to the focal plane of the combined lens groups 77, 80. In FIG. 8 the focal plane of the fixed lens and movable lens in combination is omitted for clarity but is a virtual image plane at the same position relative to the fixed lens 77 as the real image focal plane 86 in FIG. 7.

In FIG. 8 the zoom lens in its ranging configuration provides a field angle of 10° for horizontal and vertical scanning of the projected beam 38.

A comparision of FIGS. 7 and 8 shows that in the imaging configuration the projected beam 38 emerges as a tight bundle of rays 84 or 85 whereas in FIG. 7 in the ranging configuration the bundle of rays 84 or 85 spreads to fully occupy the available aperture defined by the prism 81. In other words the zoom lens 52 provides an increased exit pupil diameter in the ranging configuration and this results in a decrease in the depth of focus available in the projected beam 38.

The movable lens 80 is constructed such that the radii of the front and rear faces 82 and 83 are given by the expression $$r = \frac{tn}{n+1}$$

where r is the radius, t is the lens thickness and n is the refractive index of the lens material.

In this arrangement very little aberration is produced, the only significant aberration being pure field curvature when monochromatic light is used.

The ratio of field angles and pupil diameters at the two configurations is approximately $n^4$.

An advantage of this arrangement is that the exit pupil of the apparatus 50 including the zoom lens 52 is close to the prism 81 so that the prism can be of relatively small size. By contrast a conventional zoom lens would result in the exit pupil being spaced at a greater distance from the prism since conventional zoom lenses include a divergent lens in the final stage. An advantage of being able to use a relatively small prism in the apparatus 50 is that only limited space is available within the tube to accommodate the fibre optic bundle 53 and the rotating mechanism of the prism.

In use of the apparatus 50 to form an image of an object 28 in an inaccessible location the endoscope tube 11 is positioned with the window 56 facing the object 28 and laser beam 15 projected from the window as projected beam 38 to illuminate the object. Reflected light from the object 28 is received at the surface 54 and conducted via the fibre optic bundle 53 to the photomultiplier 27.

The scanning head 39 is set to operate in imaging mode in which scanning mirror 69 remains stationary, scanning mirror 16 is oscillated at its resonant frequency by the scanning unit 72 so as to provide horizontal scanning deflection of the projected beam 38 and the final scanning mirror 74 is scanned so as to produce a relatively slow vertical scanning motion. A raster scan is thereby produced in the projected beam 38 so that the surface of object 28 is systematically scanned by the laser beam. The output signal of photomultiplier 27 is processed by the electronic apparatus 29 to produce a television image. An image is displayed on screen 33 of object 28.

Figure 9:
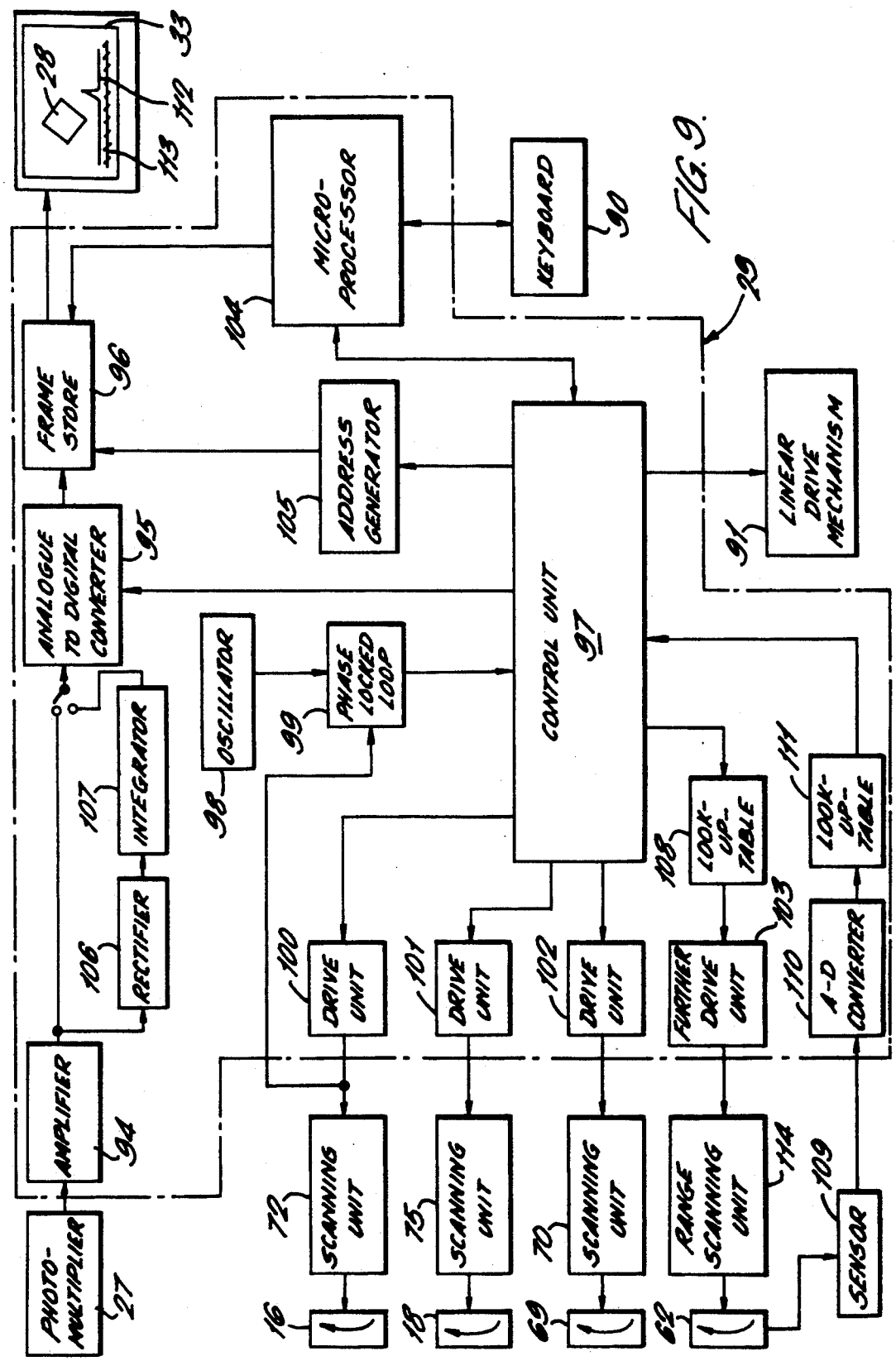
FIG. 9 is a schematic diagram of a control apparatus of the apparatus of FIG. 3.

To measure the range of object 28 from the window 56 the apparatus 50 is commanded to switch to ranging mode by an input to the electronic apparatus 29 via keyboard 90 which is used to identify coordinates of the image appearing on the screen 33 designating a portion of the object 28 at which range is to be measured. In switching to ranging mode the linear drive mechanism 91 is actuated to change the zoom lens 52 into its ranging configuration as shown in FIG. 8 which provides reduced depth of focus in the projected beam 38. The television image currently on screen 33 is stored in a frame store 96 within the electronic apparatus 29 (as represented in FIG. 9) and continues to be displayed. The horizontal and vertical scanning provided by the mirrors 16 and 18 is then discontinued and a much smaller amplitude horizontal dither in the projected beam 38 is introduced by scanning of mirror 16. The extent of dither is such as to provide scanning corresponding to a width of about five pixels in the television image.

At the same time the electronic apparatus 29 commands the prism rotating mechanism 87 and tube rotating mechanism to direct the projected laser beam 38 on to the required element of the object 28 at which range measurement is to be carried out. The range scanning unit 114 is actuated so as to oscillate the mirror system 62 and thereby cyclically vary the path length between mirror 61 and lens 68 within the scanning head 39. This has the effect of cyclically shifting the image plane positions along the optical axis of the apparatus 50 with consequent cyclical scanning in focus distance D of the focal plane 92 at which the projected beam 38 is focused.

The signal from the photomultiplier 27 is analysed throughout this motion in order to detect the value of focus distance D at which signal modulation corresponding to the speckle noise is at a maximum. This value of D is stored and is then displayed on the screen 33 on command given by the operator through the keyboard 90.

The structure of the electronic apparatus 29 is illustrated schematically in FIG. 9. In its normal imaging mode the electronic apparatus 29 passes the signal from the photomultiplier 27 through an amplifier 94 to an analogue-to-digital converter 95 from which the digitised video signal is input to a frame store 96. Each pixel of the image is represented in the frame store by a number digitised to 8-bits. A clock signal for the analog-to-digital converter 95 is received from a control unit 97. The clock signal is generated by an oscillator 98 and the clock frequency is modulated by means of a phase locked loop 99 connected to the horizontal line scanning unit 72 such that the sampling of the video signal by the analogue-to-digital converter is synchronised with the horizontal line scan. The phase locked loop 99 provides compensation for the non-linearity of the horizontal line scan resulting from the approximately sinusoidal variation in rate of scan produced by mirror 16.

The control unit 97 generates analogue signals to drive the scanning units 72, 75 and 70 by means of digitally controlled drive units 100, 101 and 102 respectively. A further drive unit 103 commands the range scanning unit 114 responsible for scanning the mirror system 62 during ranging mode operation.

The control unit 97 is interconnected with a microprocessor 104 under the command of a keyboard 90. The control unit 97 is linked to the frame store 96 via an address generator 105.

The scanning mirror 16 is oscillated at 8 KHZ and image data corresponding to an image of 512×512 pixels is generated and held in the frame store. The television image is generated by reading the image data from the frame store at a scan rate which is independent of the mirror scanning rate and is optimised to suit the television equipment used.

Switching of operation from imaging mode to ranging mode is carried out under control of the microprocessor 104 on command received from the keyboard 90. In ranging mode the amplified signal from the photomultiplier 27 is passed to a rectifier 106 and an integrator 107 before being routed to the analogue-to-digital converter 95. Each digitised signal S corresponds to the AC component of video signal integrated over the length of scan across the object provided by the dither motion of mirror 16 and corresponding to about five pixels of the image.

In switching to ranging mode the control unit 97 reduces the scanning of mirror 16 to a dither by suitable command to scanning unit 72. Oscillation of mirror 18 is arrested and scanning unit 75 set to direct the mirror 18 at the required vertical coordinate at which ranging is to be measured. The horizontal coordinate of the scanning beam is set by means of scanning unit 70 and mirror 69 which determines the mean position about which horizontal scanning dither is provided by mirror 16.

The control unit 97 commands the range scanning unit 114 to dynamically vary the focus distance D at which the projected beam 38 is focused by movement of the mirror system 62. Since the variation of D is proportional to the square of the angular position of mirror system 62 a linear scan of focus distance is achieved by processing the command signal to the drive unit 103 using a look-up table 108. The position of the mirror system 62 is sensed using a sensor 109, the output of the sensor being digitised by an analogue-to-digital converter 110 and interpreted as a signal representing range R by means of a look-up table 111.

During ranging mode operation the screen 33 displays the last recorded image frame entered into the frame store and this is schematically represented as an image 28 on the screen 33 in FIG. 12. Underneath the image a horizontally scanned trace 112 representing the signal S as a function of scanned focus distance D is displayed against a range scale 113 so that the operator can interpret the peak of the trace as a measurement of range R.

The microprocessor 104 includes software enabling the image appearing on the screen 33 to be processed using conventional image processing techniques as may be required.

The linear drive mechanism 91 for operating the zoom lens 52 is also under the control of control unit 97 and as described above the zoom lens is actuated on switching to ranging mode to provide decreased depth of field.

A number of alternative arrangements and refinements to the apparatus 50 are envisaged. For example the zoom lens 52 may be actuated during normal viewing mode to provide increased magnification if required.

The image displayed on screen 33 may alternatively be processed under the control of microprocessor 104 using conventional software techniques in a number of ways. Alphameric information may be displayed containing a description of the image viewed, the image may be enhanced or portions magnified and the range information can be represented in any convenient form. A scale may be displayed from which the dimensions of the object may be measured.

The photomultiplier may be replaced by any other suitable photodetector. Analysis of the detected light may use parameters other than the noise amplitude in the detected signal and may for example use information derived from the spacial frequency of the speckle pattern. Software may also be utilised to statistically analyse the range signal using curve fitting or digital filtering techniques in order to optimise the sensitivity of the apparatus 50.

Laser light containing more than one frequency may be used during imaging in order to obtain colour information so as to enable the displayed image to be in colour. Three separate lasers may for example be used to provide red, green and blue laser light frequencies with suitable combination optics being incorporated in the apparatus prior to scanning of the laser beam by the laser scanning head 39. Alternatively a single laser providing a number of separate discrete wavelengths may be utilised. The optical components can be optimised to minimise aberrations at the wavelengths used.

The diameter of the endoscope tube may be larger or smaller than the 10 mm tube of the described embodiments. In general a larger diameter is used when tubes of greater length are required and the typical range of diameter is between 8 and 16 mm.

The zoom lens 52 may be manually controlled as may be the prism rotating mechanism 87 and/or the tube rotating mechanism either of which may also be used to adjust the direction of use during imaging.

The scanning head 39 may include scanning mirrors arranged to deflect the beam through average angles other than 90° where this is convenient for folding the optical axis into a more compact form.

The measurement of range R may also be utilized when the apparatus is operating in imaging mode to adjust the focus of the projected beam so as to be focussed onto the object under inspection to provide improved resolution.

The side viewing arrangement of apparatus 50 may be modified to provide other directions of view.

FIG. 10 shows a modification to apparatus 50 and reference numerals corresponding to those of FIGS. 3 to 9 are used where appropriate for corresponding elements. Modified apparatus 120 of FIG. 11 has an endoscope tube 11 with a distal end 36 terminating in an end face 121 which is orthogonal to the tube 11.

A circular window 56 is provided in the end face 121 and the projected laser beam 38 exits from window 56 to eliminate an object 28. Light reflected from the object 28 is received at a light collecting surface 54 at a circular window 122 in the end face 121 and located next to the window 56.

As shown in schematic plan view in FIG. 11 the distal end 36 contains a light deflecting element 81 which is steerable by means of a rotating mechanism 87 so that in ranging mode the projected beam 38 can be steered on to a selected portion of object 28 at which range is to be measured.

The deflecting element 81 is positioned between the zoom lens 52 and window 56 and in normal imaging mode introduces zero deflection in the projected beam 38.

The windows 54 and 56 may be other than circular in shape. Preferably however both should be of the same shape and of the same order of cross-section.

The apparatus 50 may alternatively be modified to have a distal end 36 adapted for retro viewing in which the projected beam 38 is deflected by more than 90° from the forward viewing direction or alternatively may be adapted for oblique viewing in which the projected beam 38 is deflected by an angle of less than 90° from the forward viewing direction.

In each case the windows 54 and 56 may be positioned side-by-side or with window 56 located centrally and surrounded by an annular light collecting input surface 26 as shown for example in FIG. 1.

Apparatus 50 may alternatively include a conventional zoom lens as shown by way of example in FIGS. 12 and 13.

FIG. 12 shows a conventional zoom lens 130 incorporated in the distal end of an endoscope tube of apparatus in accordance with the present invention and located intermediate an optical relay 12 and a light deflecting prism or other light deflecting element 81.

The zoom lens 130 comprises a first stationary lens group 131 located immediately adjacent the prism 81 and a second stationary lens group 132 spaced intermediate the first lens group and the optical relay 12. Both lens groups 131 and 132 are arranged to be of negative (diverging) power. An axially movable lens group 133 of positive power is located intermediate the first and second lens groups 131 and 132 and is movable between a first position as shown in FIG. 12 in which it is immediately adjacent the first lens group 131 and a second position as shown in FIG. 13 in which it is immediately adjacent the second lens group 132.

With movable lens group 133 in its first position as shown in FIG. 12 the zoom lens provides a large field angle of 50° over which the projected laser beam 38 is scanned both horizontally an vertically. This configuration is used for imaging and provides considerable depth of field by virtue of the effective aperture of the lens being smaller than the aperture defined by the end window 56 so that when the projected beam is focused it has a small convergence angle.

FIG. 13 shows the conventional zoom lens 130 in its ranging configuration in which the field angle is reduced to 10° and the depth of focus considerably reduced by virtue of the effective aperture being increased to fill the end window 56 with consequent increase in the convergence angle of the projected beam when focused.

As shown in FIG. 12 the prism 81 limits the field angle because the exit pupil of a conventional zoom lens is spaced from the prism to an extent such that at the maximum deflection of the projected beam 38 some of the light is cut-off at the edges of the prism. This can be compensated to some extent by including a larger prism 81 but only limited space is available within the endoscope tube 11 which must also accommodate the fibre optic bundle 53 and the prism rotating mechanism 87. It is for this reason that the conventional zoom lens 130 is less satisfactory than the zoom lens described above with reference to FIGS. 7 and 8.

The zoom lens of FIGS. 7 and 8 may be improved by modification to the movable lens 80 so as to have front and rear optical faces 82 and 83 of dissimilar curvature as shown in broken lines in FIGS. 7 and 8. Such an asymmetric movable lens would no longer result in the laser beam 15 being focused at one or other of the optical faces 82, 83 and this would reduce the extent of degradation to the optical performance of the lens due to light scattered by any dust deposited on these optical surfaces.

The zoom lens may further be refined as shown in FIGS. 14 and 15 by replacing the single element movable lens 80 of FIGS. 7 and 8 by a multi-component movable lens group 140 which is configured to reduce curvature of field produced in the zoom lens. The movable lens 140 may also be further modified to be asymmetric. In such an asymmetric lens group (not shown) the arrangement of elements is preferably such that elements of negative power are followed by elements of positive power (i.e. the positive power elements are facing the fixed lens group 77). This results in the principal planes of the movable lens group 140 being displaced towards the fixed lens group 77.

The zoom lens 52 can be made more effective if the travel of the moving lens group 140 between its imaging and ranging configurations is maximised. In practice the limit of travel is set by mechanical interference between the movable lens group 140 and the fixed lens group 77 whereas the optical relay 12 is spaced sufficiently from the zoom lens not to have limiting effect on this travel. The effect of asymmetry described above allows the effective position of the movable lens group 140 to be closer to the fixed lens group 77 and can thereby effectively increase the available travel.

The components of the zoom lens 52 may also be corrected for chromatic aberration in known manner if it is required to use more than one laser scanning frequency or if the endoscope tube is dual purpose in that it may also be used as part of a conventional endoscope by the attachment of an eyepiece to the proximal end of the endoscope tube 11.

Curvature of field introduced by using a single element movable lens 80 may alternatively be corrected elsewhere in the optical system of the apparatus 50. For example compensating field curvature may be introduced in the laser scanning head. Normally in the apparatus 50 of FIG. 3 the laser beam 15 is presented as a collimated beam on to the scanning mirrors 16 and 18. If however the beam 15 is focused a short distance before each of the mirrors 16 and 18 such that light is diverging from a point focus when it hits each mirror 16 and 18 then curvature of field results. The field curvature introduced by the scanning head 39 and in the zoom lens 52 can then be arranged to substantially self cancel.

A further alternative modification to the apparatus 50 of FIG. 3 is shown in FIG. 16 in which corresponding reference numerals to those of FIG. 3 are used where appropriate for corresponding elements. Instead of a zoom lens 52 a beam-splitter 150 is provided such that the laser beam 15 is split into a first component 151 deflected through 90° to normally exit from the endoscope tube 11 through window 56 and a second component 152 directed through a fixed lens group 153 into a right angle prism 81 from which it is directed through a further window 154.

A shutter 155 (which is represented only schematically in FIG. 16) is provided to allow either one of the first and second beam components 151 and 152 to be selected for transmission. In FIG. 16 the shutter 155 is configured to allow the first beam component 151 to emerge from the window 56 as projected laser beam 38 and in this configuration the modified apparatus 156 of FIG. 16 is in its normal imaging configuration. To switch to ranging mode the shutter 155 is actuated to shut-off the first beam component 151 and transmit the second beam component 152. The fixed lens group 153 comprises a diverging lens followed by a converging lens having the effect of broadening the beam component 152 which after being deflected by the prism 81 is transmitted through the further window 154 as shown in broken lines in FIG. 16. This results in the projected beam having an increased convergence angle and hence a reduced depth of field as required in the ranging mode. The increased convergence angle is accompanied by a decrease in the field angle so that the prism 81 is provided with a prism rotating mechanism 87 so that in ranging mode the projected beam 38 can be targeted on any required portion of the object 28.

The zoom lens 52 as shown in FIGS. 7 and 8 or as modified in FIGS. 14 and 15 (and additionally including asymmetric movable lens and/or achromatisation as may be required) may be incorporated in a conventional endoscope 160 as illustrated schematically in FIG. 17 where corresponding reference numerals to those of the preceding Figures are used where appropriate for corresponding elements.

In FIG. 17 the endoscope 160 includes an endoscope tube 11 having a distal end 36 including components corresponding to those of the apparatus of FIG. 4. The endoscope tube 11 has a proximal end 35 connected to a housing 161 having an eyepiece 162. The endoscope 160 is also connected to a source of white light 163 by means of a light guide 164. Light from the white light source 163 is passed into the housing 161 and along a fibre optic bundle 53 to emerge from window 54 so as to illuminate the object 28. Reflected light from the object 28 is received at the window 56 and reflected by means of prism 81 into the zoom lens 52. An image of the object is transferred to the eyepiece 162 by means of the optical relay 12 where it is directly viewed by an observer. The zoom lens 52 is controlled by means of a control wire 57 extending into the housing 161 and connected to an actuator 165.

The zoom lens 52 is actuated by movement of the actuator 165 to provide switching of the zoom lens between its two alternative configurations at which different angular magnifications are provided.

Various aspects of the present invention may also be incorporated in a laser scanning camera. A conventional laser scanning camera comprises a laser light source, a scanning unit for scanning the laser beam in raster fashion so as to scan an object field, a light detector for detecting light reflected from the object field and electronic apparatus for processing the output signal of the light detector to produce a television viewable image of the object field.

Figure 18:
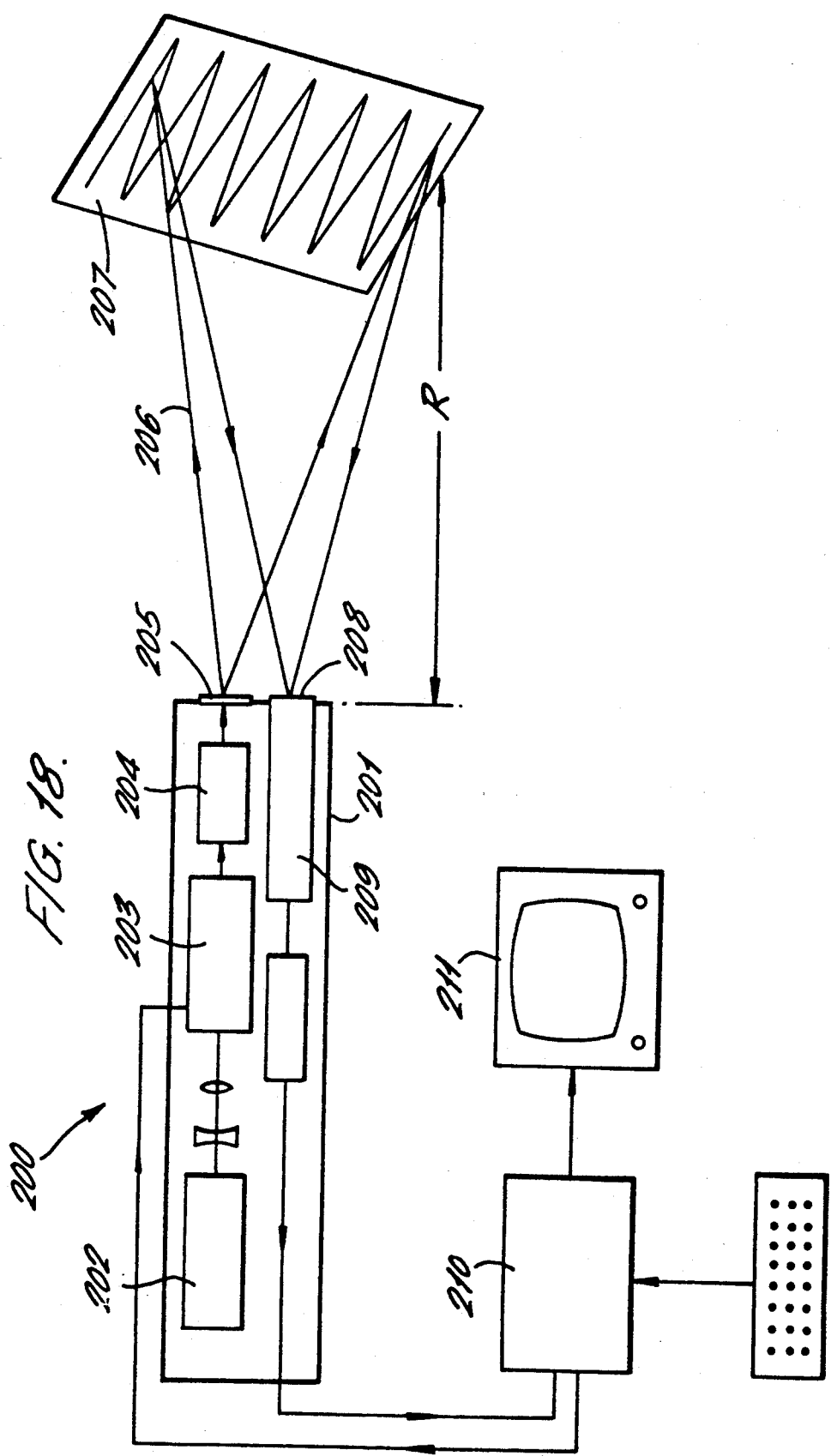
FIG. 18 is a schematic diagram of a laser scanning camera.

An improved laser scanning camera 200 is shown schematically in FIG. 18 and comprises a camera body 201 housing a laser 202 and a scanning unit 203. A scanned laser beam produced by the scanning unit 203 passes through a zoom lens 204 and finally through an end window 205 as a projected beam 206 which scans an object field 207 in raster fashion. The drawing represents rays corresponding to maximum upper and lower deflection of the beam 206 and shows the zig-zag raster pattern traversed by the beam across the object field 207.

A light receiving window 208 is arranged to collect reflected light from the object field 207 and a photomultiplier 209 detects light transmitted through the window. Electronic apparatus 210 processes the output signal of photomultiplier 209 and drives a television monitor 211 which displays an image of the object field 207. A keyboard 212 is connected to the electronic apparatus 210 for the input of control commands.

Figure 19:
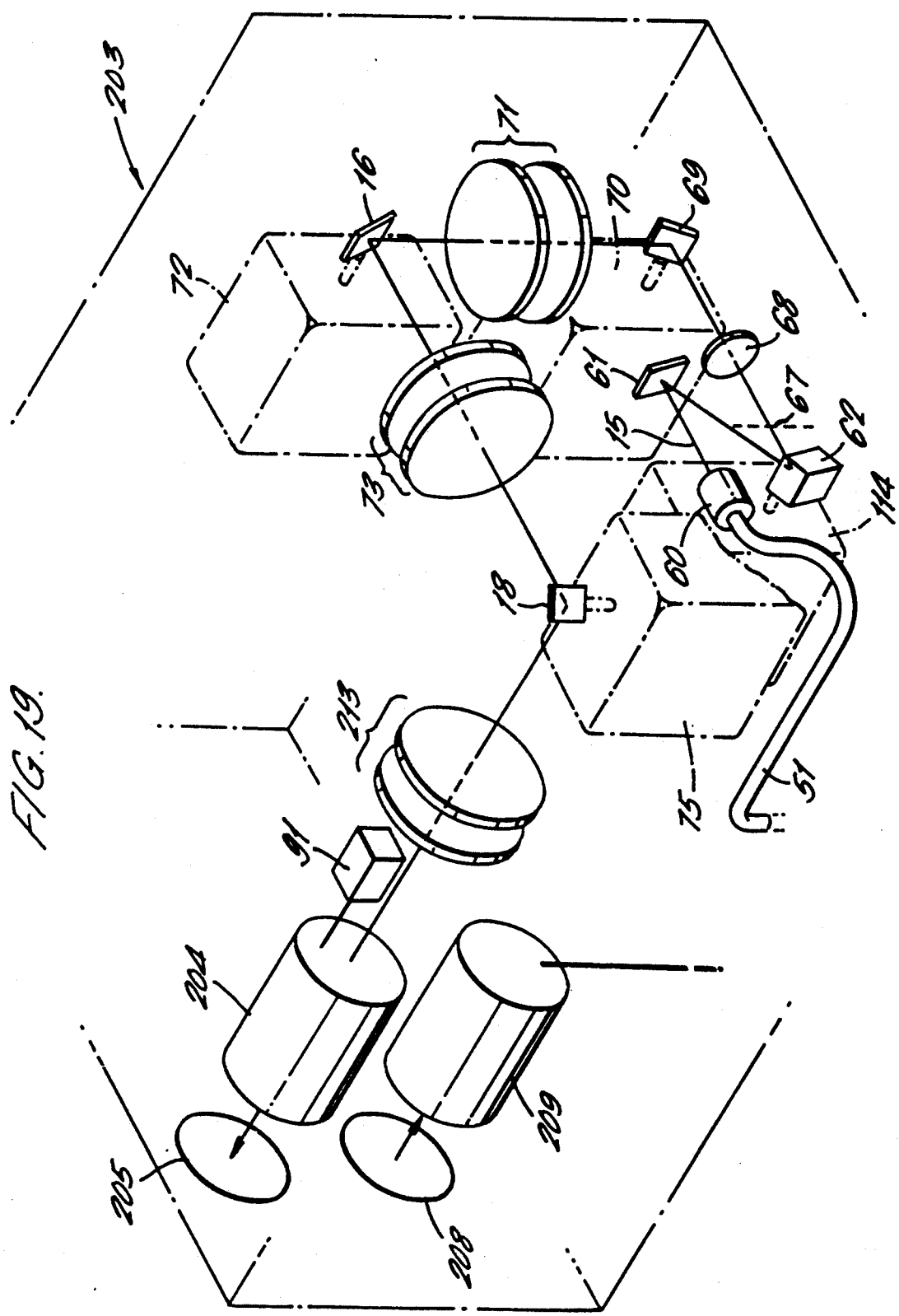
FIG. 19 is a perspective view of the scanning unit of the camera of FIG. 18.

The scanning unit 203 is similar to the laser scanning head 39 described above with reference to FIG. 5 but is modified as shown in FIG. 19 where corresponding reference numerals to those of FIG. 5 are used where appropriate for corresponding elements. FIG. 19 shows the axial light path of the laser beam after leaving the scanning mirror 18 passing through a field lens pair 213 into zoom lens 204 which is represented schematically as a cylindrical component. On emerging from the zoom lens 204 the light beam exits from the end window 205 towards the object field. The photomultiplier 209 is represented schematically as a cylinder placed immediately behind the light receiving window 208.

The zoom lens 204 is constructed in the manner described above with reference to FIGS. 7, 8, 12, 13, 14 or 15 or as modified in accordance with the various modifications discussed above.

The electronic apparatus 210 corresponds to the electronic apparatus 29 described above with reference to FIG. 9 or as modified by any of the modifications described above.

In use of the laser scanning camera 200 to form an image of the object field 207 the camera is directed such that end window 205 faces the object field and the laser beam 206 is projected on to the object field in raster fashion with the scanning unit 203 and the zoom lens 204 both in their imaging configuration. In the imaging configuration the zoom lens provides a wide field angle of 50° and a long depth of focus. The scanning unit 203 in its imaging configuration provides normal raster scanning as described above.

Image information is acquired in the frame store 96 of the electronic apparatus 210 and output to the television monitor 211.

On receipt of a ranging command from the keyboard 212 the camera is switched to its range finding mode in which the zoom lens 204 is re-configured into its ranging mode so as to provide a narrow field angle of 10° and a short depth focus. At the same time the scanning unit 203 in its ranging mode of operation is targeted on to a selected portion of the object field by positioning of mirror 69 and mirror 18 whilst providing dither in the horizontal scan direction by means of scanning mirror 16. At the same time the total range of the projected laser beam is scanned cyclically using mirror system 62.

The reflected light from the object field is detected by photomultiplier 209 and processed by electronic apparatus 210 to determine the value of focus distance D at which signal modulation corresponding to laser speckle noise is at a maximum. This value of focus distance D is stored and displayed as a measurement of range R using the monitor 211.

The method of range finding in accordance with the present invention has application in all uses of endoscopy and remote inspection particularly where an unfamiliar scene is viewed as a television image. It does not require the use of a high intensity spot illumination and can be arranged to make use of the existing imaging apparatus of a laser scanning camera or an endoscopic imaging apparatus as hereinbefore disclosed.

The imaging apparatus of the present invention also has application in all uses of remote inspection where the advantages of using a laser scanning camera can be coupled with the convenience of endoscopy. The endoscope tube of the apparatus need not contain any active electronic components and can therefore be immune to radiation hazards. The use of laser scanning avoids the need for illumination with high intensity light. The apparatus may be used to provide images using non visible radiation if required.

I claim:

1. An optical assembly comprising an objective lens and a field lens which is movable relative to the objective lens between a first position adjacent the objective lens and a second position spaced from the objective lens, the field lens and objective lens in combination defining a focal plane which is at the same location relative to the objective lens for both first and second positions of the field lens and wherein the field lens passes through the focal plane in moving between the first and second positions.

2. An optical assembly as claimed in claim 1 wherein at least one of the field lens and the objective lens comprises a plurality of lens elements.

3. An optical assembly as claimed in claim 1 wherein the field lens comprises a single thick element.

4. An optical assembly as claimed in claim 1 wherein the objective lens and the field lens are both of positive power.

5. An optical assembly as claimed in claim 1 wherein the field lens is asymetric.

6. An optical assembly as claimed in claim 1 wherein the field lens and objective lens in combination comprise a zoom lens arranged in series with an optical relay of an endoscope.

* * * * *